United States Patent [19]

Lane

[11] Patent Number: 5,405,379
[45] Date of Patent: Apr. 11, 1995

[54] SELF EXPANDING VASCULAR ENDOPROSTHESIS FOR ANEURYSMS

[76] Inventor: Rodney J. Lane, Greenwich Square, 130-134 Pacific Highway, St. Leonards, NSW, Australia, 2065

[21] Appl. No.: 977,440
[22] PCT Filed: Jul. 23, 1991
[86] PCT No.: PCT/AU91/00326
  § 371 Date: Feb. 24, 1993
  § 102(e) Date: Feb. 24, 1993
[87] PCT Pub. No.: WO92/01425
  PCT Pub. Date: Feb. 6, 1992

[30] Foreign Application Priority Data
  Jul. 26, 1990 [AU] Australia ............... PK1374

[51] Int. Cl.⁶ .................... A61F 2/06; A61F 2/04
[52] U.S. Cl. ........................................ 623/1; 623/12
[58] Field of Search .......... 623/1, 12; 606/194, 606/195; 600/36

[56] References Cited

U.S. PATENT DOCUMENTS

| | | | |
|---|---|---|---|
| 4,140,126 | 2/1979 | Choudhury | 623/1 |
| 4,550,447 | 11/1985 | Seiler, Jr. et al. | 623/1 |
| 4,562,596 | 1/1986 | Kornberg | 623/1 |
| 4,617,932 | 10/1986 | Kornberg | 623/1 |
| 4,740,207 | 4/1988 | Kreamer | 623/1 |
| 5,078,726 | 1/1992 | Kreamer | 623/12 |
| 5,167,614 | 12/1992 | Tessmann et al. | 623/1 |
| 5,171,262 | 12/1992 | MacGregor | 623/12 |
| 5,192,307 | 3/1993 | Wall | 623/12 |

OTHER PUBLICATIONS

R. J. Lane. "The treatment of abdominal aortic . . ." Project report submitted as part of requirement for degree in Master of Biomedical Engineering, University of South Wales, 1993. Whole thesis.

Primary Examiner—Randall L. Green
Assistant Examiner—Debra S. Brittingham
Attorney, Agent, or Firm—Nixon & Vanderhye

[57] ABSTRACT

A self expanding vascular endoprosthesis for aneurysms comprising a sheet of a resiliently flexible biocompatible material, such as polypropylene which sheet has been rolled upon itself about one of its longitudinal edges. The tightly rolled endoprosthesis is introduced in the end of the catheter through a contiguous artery into the artery having the aneurysm. After ejection from the catheter at a suitable point in the artery the endoprosthesis expands to form a bridge isolating the aneurysm from the arterial blood flow. The endoprosthesis stimulates cellular proliferation in the adjacent vascular tissue which assists in forming a seal between the endoprosthesis and the vascular tissue. The resultant endothelial growth also assists in maintaining the endoprosthesis in position in the artery.

6 Claims, 3 Drawing Sheets

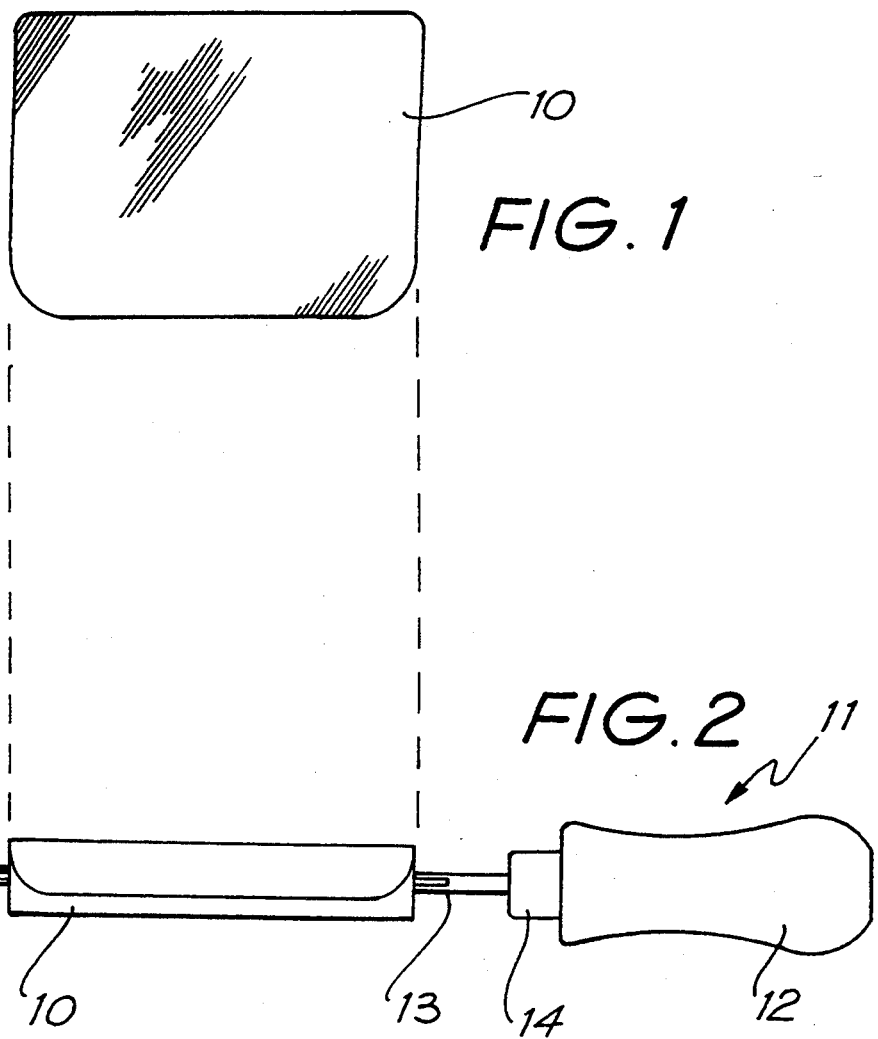

SELF EXPANDING VASCULAR ENDOPROSTHESIS FOR ANEURYSMS

FIELD OF THE INVENTION

The present invention relates to a self expanding vascular endoprosthesis for aneurysms and to apparatus and a method for introducing such an endoprosthesis into an artery.

BACKGROUND ART

An Aneurysm is the focal abnormal dilation of an artery. The complications which arise from aneurysms are specifically rupture, embolisation, fistularisation and symptoms related to pressure on surrounding structures. Aneurysms are commonly found in the abdominal aorta, being that part of the aorta which extends from the diaphragm to the point at which the aorta bifurcates into the common iliac arteries. These abdominal aortic aneurysms typically occur between the point at which the renal arteries branch from the aorta and the bifurcation of the aorta.

The standard treatment for aneurysms is to resect them by opening the aneurysm directly and inserting an inlaid graft made of a biocompatible material such as Dacron. The operation in most cases is large entailing considerable blood loss, at least 10 days in hospital and a mortality rate of about 5% in elective cases. This mortality rate is normally related to associated vascular problems such as myocardial infarction. Many patients cannot be subjected to such a large procedure because of intercurrent disease and therefore die of the aneurysm or the complications thereof.

It has been proposed by Balka etal. (Journal of Surgical Research 40 305-309 (1986)) to treat abdominal aortic aneurysms by the insertion of an intraluminal prosthesis, which approximates the diameter of the aorta above and below the aneurysm, into the aorta through the common femoral artery. In this case the prosthesis comprised a polyurethane tube with a nitinol and/or stainless steel frame which was designed in such a configuration that it can be compressed inside a catheter and then regain its original shape after being discharged into the aorta. This proposal does not appear to have been adopted for the treatment of humans due to difficulty in ensuring that the prosthesis will expand sufficiently to form a seal with the aorta above and below the aneurysm. The present inventor has developed a prosthesis which provides an alternative to that proposed by Balka et al.

In a first aspect the present invention consists in a self expanding vascular endoprosthesis adapted to bridge across an aneurysm in an artery, the endoprosthesis comprising a substantially imperforate sheet of a resiliently flexible biocompatible material, the sheet being rolled upon itself about one of its longitudinal edges, the material from which the sheet is formed being such that (a) upon being introduced into an artery the endoprosthesis will resiliently expand of its own volition to press firmly against the internal wall of the artery to bridge across the aneurysm and to fluid isolate it from blood flowing in the artery, and (b) the endoprosthesis has sufficient longitudinal stiffness that there will be a compliance mismatch between the endoprosthesis and the wall of the artery to induce sufficient cellular proliferation in that wall adjacent the ends of an implanted endoprosthesis to cause the endoprosthesis to be adhered to the arterial wall.

In a second aspect the present invention consists in apparatus for introducing a self expanding vascular endoprosthesis for aneurysms into an artery, comprising an elongate tubular catheter, a self expanding vascular prosthesis for aneurysms according to the present invention disposed within the catheter and means for ejecting the endoprosthesis from the catheter.

In a third aspect the present invention consists in a method for treating an aneurysm in an artery by introducing a self expanding endoprosthesis into the artery, the method comprising the steps of:

inserting one end of a catheter containing a self expanding vascular endoprosthesis according to any one of claims 1 to 5 into an artery communicating with the artery having the aneurysm, moving the catheter along the patient's vascular system until the end of the catheter is adjacent the aneurysm, ejecting the endoprosthesis from one end of the catheter such that it bridges across the aneurysm and expands firmly into contact with the wall of the artery so that the aneurysm is fluid isolated from blood flowing in the artery, and causing the endoprosthesis to be held in position bridging across the aneurysm by cellular proliferation of the wall of the artery caused by the compliance mismatch between the endoprosthesis and the wall of the artery.

The endoprosthesis is preferably formed from a substantially rectangular sheet of a suitable grade of polypropylene or another similar synthetic plastics material. The sheet preferably has a thickness of from 0.01 mm to 0.8 mm, more preferably 0.3 mm to 0.5 mm. The corners of the sheet which are on the outside of the prosthesis are preferably rounded to avoid ulceration of the arterial wall. The length of the sheet must be sufficient to bridge the aneurysm but is preferably sufficient that one end rests against a bifurcation of the artery in which the aneurysm occur. This latter preferment assists in retention of the endoprosthesis in a position in which it bridges over the aneurysm. still allowing blood supply to the diverging vessels.

In another embodiment of the invention the endoprosthesis is such that upon release from the end of the catheter it is capable of increasing in length as well as expanding radially outwardly. The sheet forming the endoprosthesis might have a "memory" causing it to want to expand from its rolled up cylindrical form into a helical form of greater diameter than the initial cylinder and of greater length. The overlapping turns of the expanded helical coil serving to prevent fluid communication between the interior of the endoprosthesis and the aneurismal sac. In another form of the invention the sheet forming endoprosthesis may be of a very thin film having ribs which assume a helical form when released from the endoprosthesis. The advantage of an endoprosthesis which can increase in length after release from the catheter is that it is easier to thread a catheter containing such a shortened endoprosthesis through the patient's vascular system to the point of the aneurysm.

The sheet of material from which the endoprosthesis is rolled up preferably has a compliance mismatch with the vascular tissue and is preferably quite stiff in a longitudinal direction. This is believed to have the effect of stimulating a reaction in the arterial wall and thereby inducing cellular proliferation in the vascular tissue surrounding the ends of the endoprosthesis. This causes a proliferation of endothelial cells which has the effect of adhering the endoprosthesis to the arterial wall. The endoprosthesis thus has a self suturing effect which retains it against movement along the artery.

The material from which the endoprosthesis is formed should be resiliently flexible so that upon being released from the constraint of the catheter the prosthesis will expand to bear against the arterial wall above and below the aneurysm. The use of the sheet of material rolled up along one of its side edges to form a scroll has been found to allow the prosthesis to expand very considerably if need be. This feature is important because the neck of the aneurysms tend to vary greatly between patients. Also depending upon where the ends of the endoprosthesis extend to the size of the native artery may be quite small or quite large. It is important that the endoprosthesis does not occlude vessels extending laterally from the artery and thus it may be necessary to terminate the endoprosthesis in a mildly distended part of the aneurysm. For this reason it may be necessary for the endoprosthesis to expand not merely to the normal diameter of the artery but to whatever extent is necessary to form a seal with the artery at either end of the aneurysm so that systalic blood pressure is not transmitted to the aneurysmal sac formed between the endoprosthesis and the distended arterial wall.

In the case of the abdominal aorta the normal internal diameter of the aorta is about 18 mm. Abdominal aortic aneurysms will typically have a diameter of from 40 to 70 mm. The abdominal aorta between the renal arteries and the iliac arterial bifurcation is typically about 110 mm. The aneurysm normally extends along a substantial portion of the abdominal aorta and is bounded at either end by a neck of undistended arterial wall adjacent the renal arteries and adjacent the iliac arterial bifurcation. In this case then the prosthesis is preferably rolled up from a sheet of polypropylene having a thickness of 0.4 mm, a length of 110 mm and a width of from 98 mm to 142 mm. It should be recognized however that the neck of the aneurysms tend to be very variable and it may be necessary to use a sheet wider than that indicated to form the endoprosthesis.

The present inventor has found that the endoprosthesis according to the present invention may be rolled up to a very small diameter allowing its introduction into a deep artery, such as the abdominal aorta, from a more superficial but much smaller artery, such as the common femoral artery.

The apparatus according to the present invention comprises a conventional catheter into which the endoprosthesis has been inserted in a rolled up condition and means to eject the endoprosthesis from an end of the catheter. The apparatus may also include a guide wire and/or sensing means to assist in the determination of the correct position at which the endoprosthesis should be ejected from the catheter. The ejection of the endoprosthesis from the catheter may be achieved by holding the catheter stationary and pushing the endoprosthesis from it using a plunger extending down the catheter or the plunger may be abutted against the proximal end of the endoprosthesis and the catheter withdrawn from around the endoprosthesis.

BRIEF DESCRIPTION OF THE DRAWINGS

Hereinafter given by way of example is a preferred embodiment of the present invention described with reference to the accompanying drawings in which:

FIG. 1 is a front elevational view of a sheet of material suitable for forming into a self expanding vascular endoprosthesis according to this invention;

FIG. 2 is a perspective view of the sheet of FIG. 1 which has been rolled into the form of a self expanding vascular endoprosthesis according to this invention on a suitable forming tool;

BEST METHOD

Figure 3:
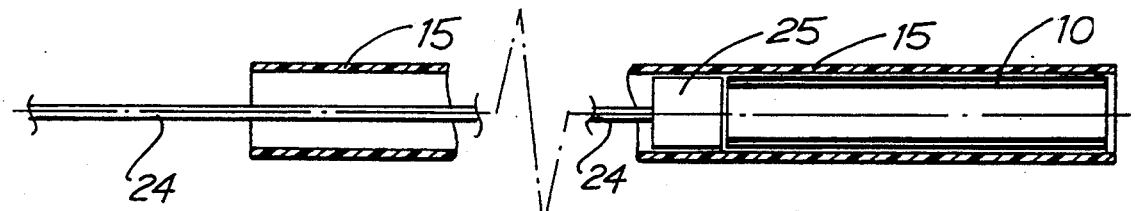
FIG. 3 is a longitudinal sectional view of a catheter containing a self expanding vascular endoprosthesis according to this invention and a device for ejecting the prosthesis from the catheter.

The sheet 10 of FIG. 1 is formed of surgical grade, imperforate polypropylene having a thickness of 0.4 mm, a width of 120 mm and a length of 110 mm with rounded corners. The sheet 10 is preferably rolled up into a self expanding vascular endoprosthesis on a tool 11 having a handle 12 and, extending axially from it, a bifurcated rod 13. A sleeve 14 is slidable disposed on the rod 13. In use one side edge of the sheet 10 is slid between the bifurcation of the rod 13 and the tool 12 rotated to roll the sheet 10 about the rod 13. After being tightly rolled onto the rod 13 the sheet 10, now formed into an endoprosthesis, is inserted into the proximal end of a suitable catheter 15. The tool 12 can then be disengaged from the endoprosthesis 10 by positioning the collar 14 against the end of the endoprosthesis 10 and withdrawing the rod 13 from within the rolled up endoprosthesis 10. The endoprosthesis 10 is now ready for insertion into a patient.

Figure 4:
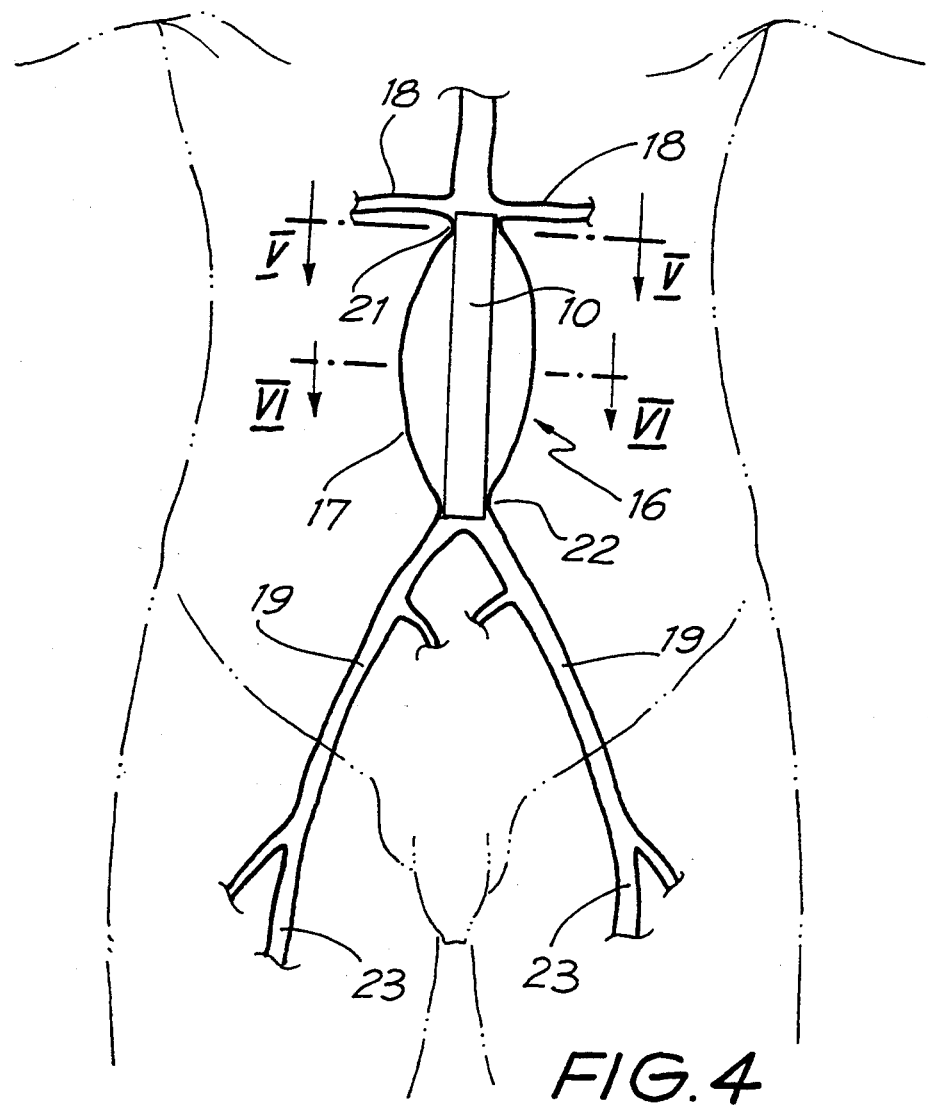
FIG. 4 is a diagrammatic ventral view of a patient showing a vascular endoprosthesis according to the invention in position spanning an abdominal aortal aneurysm.

FIG. 4 shows a typical abdominal aortic aneurysm into which an endoprosthesis 10 has been inserted. The abdominal aorta 16 has become distended to from an aneurysm 17 between the renal arteries 18 and the point at which the aorta 16 bifurcates to form the left and right iliac arteries 19. The endoprosthesis 10 is introduced to bridge the aneurysm 17 between a neck 21 adjacent the renal arteries 18 and a neck 22 adjacent the iliac arteries 19. This introduction is achieved by giving the patient a local anaesthetic in the region of one of the common femoral arteries 23 and introducing the catheter 15 through that artery and through the contiguous iliac artery into the aorta 16. The position of the tip of the catheter 15 relative to the renal arteries 18 needs to be known accurately to prevent the endoprosthesis 10 being introduced into the aorta 16 at a level where its upper end will occlude the renal arteries or where its lower end will expand in one of the iliac arteries 19. This is achieved in a manner known per se by angiography or by the introduction of an endoscope or some other form of inter-luminal or transcutaneous imaging system (not shown) through the catheter 15.

Figure 5:
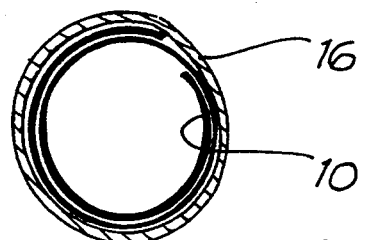
FIG. 5 is a cross-sectional view along V—V of FIG. 4.
Figure 6:
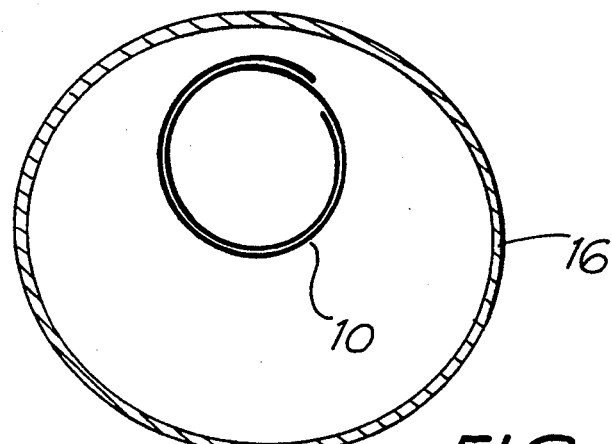
FIG. 6 is a cross-sectional view along VI—VI of FIG. 4.

After the tip of the catheter 15 has been correctly positioned in the aorta 16 the endoprosthesis is ejected from the catheter 15 into the aorta 16. This is preferably achieved by positioning an ejector 24 in the catheter 15 with an end portion 25, which forms a close sliding fit with the catheter 15, abutting against the end of the endoprosthesis 10. The catheter 15 is then carefully withdrawn. As it is ejected from the catheter 15 the natural resilience of the endoprosthesis 10 causes it to expand until it bears firmly against the aorta 16 at its narrowest points, in this case the neck 25, portions 21 and 22 (see FIG. 5). The expanded endoprosthesis 10 will form a tube bridging the aneurysm 17 to form an aneurysmal sac between the endoprosthesis 10 and the aorta 16 in the region of the aneurysm 17 which is not in fluid communication with the arterial blood flow (see FIG. 6).

It is believed that the stiffness of the synthetic plastics material from which the endoprosthesis 10 is formed will induce cellular proliferation in the aortal wall adjacent the ends of the endoprosthesis 10. This cellular proliferation assists in holding the endoprosthesis 10 in place in the aorta 16.

Figure 7:
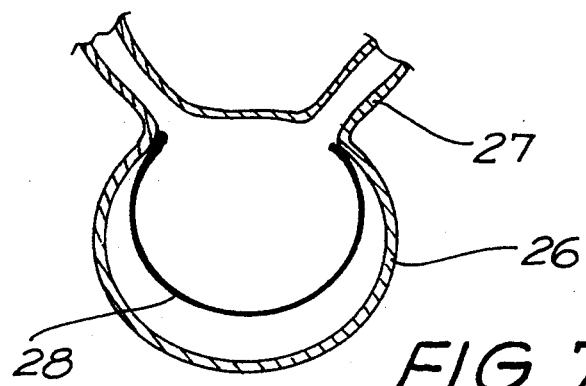
FIG. 7 is a cross-sectional view of a self expanding vascular endoprosthesis according to the present invention in position in the thoracic aorta of a patient.

As is seen in FIG. 7, if it is desired to preserve blood flow from an artery 26, such as the thoracic aorta, into a diverging blood vessel 27, such as the spinal artery, an endoprosthesis 28 may be introduced into the artery 26 which has a width less than the circumference of the artery. In this case the isolation of the aneurysm from the arterial blood flow relies upon the endoprosthesis forming a seal with the inside of the artery 26 on either side of the diverging blood vessels 27.

It can be seen from the foregoing that the use of the endoprosthesis according to this invention, and the method according to this invention can dramatically simplify the treatment of aneurysms. It also allows treatment of patients with concurrent disease states which would not otherwise be amendable to treatment at all.

I claim:

1. A self expanding vascular endoprosthesis adapted to bridge across an aneurysm in an artery, the endoprosthesis comprising a substantially imperforate sheet having at least one longitudinal edge and being made of a resiliently flexible biocompatible material, the sheet being rolled upon itself about a longitudinal edge to form an endoprosthesis having two ends, one at either end of the longitudinal edge, the sheet having an inner surface and an outer surface each of which is smooth and free of ribs or other projections that would impede the resilient expansion of the endoprosthesis into contact with an internal wall of the artery both above and below the aneurysm, the material from which the sheet is formed being such that (a) upon being introduced into an artery the endoprosthesis will resiliently expand due to its resilient flexibility to press firmly against an internal wall of the artery both above and below the aneurysm to bridge across the aneurysm and to fluid isolate it from blood flowing in the artery, and (b) the endoprosthesis having sufficient longitudinal stiffness such that there will be a compliance mismatch between the endoprosthesis and a wall of the artery to induce sufficient cellular proliferation in that arterial wall adjacent the ends of an implanted endoprosthesis to cause the endoprosthesis to be adhered to the arterial wall.

2. An endoprosthesis as claimed in claim 1, in which the endoprosthesis is formed from a sheet of a synthetic plastics material.

3. An endoprosthesis as claimed in claim 2, in which the endoprosthesis is formed from a sheet of polypropylene having a thickness of from 0.01 to 0.8 min.

4. An endoprosthesis as claimed in claim 3, in which the endoprosthesis is formed from a sheet of polypropylene having a thickness of from 0.3 to 0.5 min.

5. An endoprosthesis as claimed in claim 1, in which the sheet is substantially rectangular having two substantially parallel longitudinal edges and has a width, as measured between the longitudinal edges, of from 1.75 to 2.5 times the circumference of the artery into which the endoprosthesis is to be introduced, which circumference is measured above the aneurysm.

6. An endoprosthesis as claimed in claim 5, which the circumference is measured below the aneurysm.

* * * * *